(12) United States Patent
Matsutani et al.

(10) Patent No.: US 7,458,494 B2
(45) Date of Patent: Dec. 2, 2008

(54) SURGICAL STAPLER WITH SOUND PRODUCING MECHANISM TO SIGNAL THE COMPLETION OF THE STAPLING PROCESS

(75) Inventors: Kanji Matsutani, Utsunomiya (JP); Masatoshi Fukuda, Utsunomiya (JP); Toshiharu Kamei, Utsunomiya (JP); Takashi Ina, Utsunomiya (JP)

(73) Assignee: MANI, Inc., Tochigi (JP)

( * ) Notice: Subject to any disclaimer, the term of this patent is extended or adjusted under 35 U.S.C. 154(b) by 42 days.

(21) Appl. No.: 11/357,814

(22) Filed: Feb. 21, 2006

(65) Prior Publication Data

US 2006/0191974 A1    Aug. 31, 2006

(30) Foreign Application Priority Data

Feb. 28, 2005  (JP) .............................. 2005-052330

(51) Int. Cl.
*A61B 17/068*  (2006.01)
(52) U.S. Cl. ...................... 227/175.1; 227/19
(58) Field of Classification Search ............. 227/181.1, 227/175.1, 19, 120, 176.1
See application file for complete search history.

(56) References Cited

U.S. PATENT DOCUMENTS

| | | | | |
|---|---|---|---|---|
| 2,707,783 | A | * | 5/1955 | Sullivan ................... 72/409.05 |
| RE28,932 | E | * | 8/1976 | Noiles et al. ................... 227/19 |
| 4,202,480 | A | * | 5/1980 | Annett ........................ 227/8 |
| 4,391,401 | A | * | 7/1983 | Moshofsky ................... 227/19 |
| 4,470,532 | A | * | 9/1984 | Froehlich ..................... 227/19 |
| 4,477,007 | A | * | 10/1984 | Foslien ....................... 227/19 |
| 4,506,670 | A | * | 3/1985 | Crossley ................... 227/181.1 |
| 4,527,724 | A | * | 7/1985 | Chow et al. ..................... 227/8 |
| 4,619,262 | A | * | 10/1986 | Taylor ..................... 227/177.1 |
| 4,634,035 | A | * | 1/1987 | Li et al. ........................ 227/19 |
| 4,662,555 | A | * | 5/1987 | Thornton ..................... 227/19 |
| 4,664,305 | A | * | 5/1987 | Blake et al. ................... 227/19 |
| 4,807,628 | A | * | 2/1989 | Peters et al. ............. 227/176.1 |
| 5,022,579 | A | * | 6/1991 | Matsutani et al. ......... 227/177.1 |
| 5,038,991 | A | * | 8/1991 | Thornton ..................... 227/19 |
| 5,080,275 | A | * | 1/1992 | Heimerl et al. .......... 227/176.1 |
| 5,137,198 | A | * | 8/1992 | Nobis et al. .............. 227/175.3 |
| 5,143,269 | A | * | 9/1992 | Matsutani et al. ......... 227/177.1 |

(Continued)

FOREIGN PATENT DOCUMENTS

JP     H05-003879 A    1/1993

(Continued)

*Primary Examiner*—Stephen F Gerrity
(74) *Attorney, Agent, or Firm*—Joseph P. Farrar

(57) ABSTRACT

A surgical stapler has a body capable of containing a plurality of staples in an aligned state; a ram provided inside the body, having a central concave portion and pressure armatures on both sides of the concave portion; an anvil that, when the armatures of the ram contact both sides of a crown of a staple, forces the center of the crown into the concave portion of the ram; and a trigger rotatably supported on the body so as to cause relative movement between the ram and the anvil. The trigger as a moving member and the body as another member strike each other so as to produce a sound and/or a vibration indicating that a staple sandwiched between the ram and the anvil is bent by the advance of the anvil into the concave portion of the ram and bending of the staple is completed.

1 Claim, 4 Drawing Sheets

U.S. PATENT DOCUMENTS

| | | | |
|---|---|---|---|
| 5,170,926 A * | 12/1992 | Ruckdeschel et al. | 227/177.1 |
| 5,181,645 A * | 1/1993 | Matsutani et al. | 227/19 |
| 5,240,164 A * | 8/1993 | Murray et al. | 227/175.3 |
| 5,497,933 A * | 3/1996 | DeFonzo et al. | 227/175.1 |
| 5,685,474 A * | 11/1997 | Seeber | 227/179.1 |
| 5,697,543 A * | 12/1997 | Burdorff | 227/176.1 |
| 5,938,101 A * | 8/1999 | Izuchukwu et al. | 227/176.1 |
| 6,601,748 B1 | 8/2003 | Fung et al. | |
| 6,817,508 B1 * | 11/2004 | Racenet et al. | 227/176.1 |
| 2006/0243774 A1 * | 11/2006 | Matsutani et al. | 227/82 |
| 2006/0278680 A1 * | 12/2006 | Viola et al. | 227/176.1 |

FOREIGN PATENT DOCUMENTS

JP   2000-217829 A   8/2000

\* cited by examiner

SURGICAL STAPLER WITH SOUND PRODUCING MECHANISM TO SIGNAL THE COMPLETION OF THE STAPLING PROCESS

BACKGROUND OF THE INVENTION

1. Field of the Invention

The present invention relates to a surgical stapler for suturing tissue, and more particularly, to a surgical stapler that enables the user to sense clearly the suturing operation, that is, the completion of the bending of the staple.

2. Background of the Invention

In surgical operations, metal staples are bent to suture shut an incision. As that which is used for this purpose, the surgical staplers described in Japanese Laid-Open Patent Application Publication No. Heisei 05-3879 and Japanese Laid-Open Patent Application Publication No. 2000-217829 are conventionally known.

FIG. 3 shows the process of bending a staple using these conventionally known surgical staplers.

A staple 1 penetrates the tissue and remains imbedded in the tissue until the incision heals. Accordingly, it is important that the staples be both sufficiently strong and do not adversely affect the tissue, and for these reasons austenitic stainless steel, which does not rust, is used for the staple 1. The staple 1 consists of rounded wire with a diameter of approximately 0.5 mm that is cut and then bent in the shape of a "C". The straight portion of the staple 1 is called the crown 1a and the portions bent from both ends of the crown 1a are called the legs 1b. In order to pierce tissue easily the tips of the legs 1b are pointed.

FIG. 3A shows an initial state, with a ram 3 moving toward an anvil 4 and the staple 1 held between the anvil 4 and the tips of pressure armatures 3a formed on both sides of a concave part 3b of the ram 3.

FIG. 3B shows an intermediate state, in which the ram 3 further descends, the anvil 4 reaches the entrance to the concave part 3b, and the staple 1 is partially bent by the armatures 3a.

FIG. 3C shows a final state, in which the ram 3 continues to descend, the anvil 4 enters the concave part 3b and presses against the crown 1a of the staple 1 at the concave part bottom surface 3b', and the staple 1 is bent at right angles at both ends of the anvil 4 in the direction of the breadth of the anvil 4, closing the staple 1. This state is the state in which the bending of the staple 1 is completed. In this state, the crown 1a indicates the top part of the staple, which is now a rectangular shape.

In the process of moving from the state shown in FIG. 3B to the one shown in FIG. 3C, the tips of the staple 1 enters the tissue, completing one suture. If the incision is a large one, suturing is repeated as many times as needed. It should be noted that, in this specification, the staple in its closed state indicates a state in which, when the staple is bent between the ram and the anvil, the most fully bent portion is completely bent, and includes not only a state in which the tips of the legs 1b of the staple 1 are completely in contact but also are just slightly separated from each other.

The surgical stapler described in Japanese Laid-Open Patent Application Publication No. Heisei 05-3879 arranges a plurality of C-shaped staples in an aligned state astride the top of the anvil plate inside the body of the stapler and pushes the staples forward with a torsion spring. The forward edge of the anvil plate is the anvil, with the ram disposed substantially perpendicular to the anvil. The anvil is fixed, and the ram is advanced toward and withdrawn from the anvil by a rotary trigger, bending the staple fed to the front of the anvil into its final rectangular shape.

The surgical stapler described in Japanese Laid-Open Patent Application Publication No. 2000-217829 has a magazine containing a plurality of staples in a state of alignment, and a ram and an anvil that are moved in tandem by a trigger. Operating the trigger causes the ram and the anvil to pick out a single staple, hold it, and move together to bend the staple into its final form.

FIG. 4 is a diagram showing an external view of a surgical stapler 10 described in Japanese Laid-Open Patent Application Publication No. Heisei 05-3879. The same ram and anvil as shown in FIGS. 3A, 3B and 3C are contained in the stapler body 11, together with a plurality of staples 1. As the trigger 12 approaches the body 11, the forward edges of the ram and the anvil approach each other within the body 11, bending the staple held at the front of the anvil into its final form.

FIG. 5 is a diagram showing the structure of a surgical stapler 20 described in Japanese Laid-Open Patent Application Publication No. 2000-217829. The surgical stapler 20 comprises a magazine 22 containing a plurality of staples 1 in a state of alignment, a ram 23, an anvil 24 and a trigger 25 inside the staple body 26.

The trigger 25 revolves around a revolving shaft 27 provided on the body 26. A hole that engages the revolving shaft 27 is a slot 28. A pin 29 and a V-shaped groove 30 guide the trigger 25 as it revolves. Such a structure enables the trigger 25 to move and revolve with respect to the body 26 of the stapler, such that when force is applied to the trigger 25, the trigger can rotate as its axis of rotation moves toward the ram 23. As a result, the distance from the axis of rotation of the trigger 25 to the grip widens, enabling a large torque to be generated with a relatively small force.

However, the surgical staplers described in Japanese Laid-Open Patent Application Publication Nos. 5-3879 and 2000-217829 suffer from the drawback that the user gets no particular sensation indicating that the staple has been bent into its final form when that action is completed as shown in FIG. 3C. At most, just prior to completion of the bending of the staple into its final form, the movement of the trigger 25 becomes easier than it has been up to that point, and then becomes harder, which is the only indication that the suture is completed. However, after the movement of the trigger 25 gets easier it is not easy to tell how hard the movement will become, and it is easy to think that the suture is completed when in fact it is not.

SUMMARY OF THE INVENTION

Accordingly, the present invention is conceived as a solution to the above-described problems of the conventional art, and has as its object to provide a surgical stapler that enables the user to sense clearly the suturing operation, that is, the completion of the bending of the staple.

To achieve the above-described object, the present invention provides a surgical stapler comprising:

a body capable of containing a plurality of staples in an aligned state;

a ram provided inside said body, having a central concave portion and pressure armatures on both sides of the concave portion;

an anvil that, when the armatures of said ram contact both sides of a crown of a staple, forces the center of the crown into the concave portion of the ram; and a trigger rotatably supported on the body so as to cause relative movement between the ram and the anvil, a moving member striking another member so as to produce a sound or a sensation of impact after a staple sandwiched between the ram and the anvil is bent by the advance of the anvil into the concave portion of the ram and bending of the staple is completed.

In addition, preferably, after bending of the staple is completed, a load on the staple from the ram increases while the positions of the ram and the anvil do not change, and the positions of the ram and the anvil can no longer be maintained and thus shift to new positions when the load reaches a certain level, such change causing a moving member to strike another member.

The moving members may include, for example, the trigger, ram or anvil. The other member, which is a strikable member, is located on the trajectory of the moving member such as the trigger, ram or anvil, and consists of the stapler body if the moving member is the trigger and consists of the anvil if the moving member is the ram.

In addition, preferably, the staples are circular in cross-section, a front edge of a bottom surface of the concave portion of the ram has a slanted surface, a ridge line of a front edge of said slanted surface contacting a staple on the anvil at a position offset to the rear of a center line of the staple, the ridge line of the front edge of the slanted surface of the ram further pressing the crown of the staple when the surgical stapler is closed, such that the ram slides across a front surface of the staple and strikes the anvil so as to produce a sound or a sensation of impact.

The above-described structure works as follows:

When the staple is bent, at first, such deformation (bending) of the staple proceeds substantially proportionally to the load exerted on the staple. However, as deformation proceeds, the load reaches its maximum and thereafter begins to decline, but deformation of the staple continues. At this point, the trigger begins to move very easily and then gets harder to pull, and when force is applied against this resistance of the trigger the surgical stapler is closed. If at this point the surgical stapler is constructed so that the trigger and the body contact each other, then when bending of the staple into its final form is completed the trigger strikes the body and produces a vibration or a sound of impact.

As a construction in which the ram and the anvil strike each other, there is one in which a front edge of the bottom surface of the concave portion of the ram is a slanted surface. Just before the bending of the staple is completed, the ridge line of the ram front edge side of the slanted surface contacts the round staple on the anvil at a point just below and behind the top of the staple. The force applied to the trigger is transmitted directly to the staple, pressing the staple against the anvil, but as the force on the trigger increases, the ram quickly slips over the surface of the staple, the slanted surface contacts the staple, the staple is pushed out of the surgical stapler along the slanted surface and the ram strikes the anvil with force, producing a sound or vibration of impact. Moreover, the staple is securely expelled to the outside of the surgical stapler by the slanted surface.

It should be noted that, alternatively, the surgical stapler may be constructed so that the ram and the anvil do not strike each other but instead remain a slight distance apart, while the trigger strikes another member such as the body of the surgical stapler.

According to the present invention, when the bending of the staple into its final form is completed, one member strikes another member so as to produce a vibration or a sound, thereby enabling the user of the surgical stapler to sense clearly that suturing is completed so as to prevent stopping of the stapling before the staple is fully bent in place and the suture is completed.

Other features, objects and advantages of the present invention will be apparent from the following description when taken in conjunction with the accompanying drawings, in which like reference characters designate the same or similar parts throughout the figures thereof.

DETAILED DESCRIPTION OF THE PREFERRED EMBODIMENTS

Preferred embodiments of the present invention will now be described in detail, with reference to the accompanying drawings.

Figure 1A:
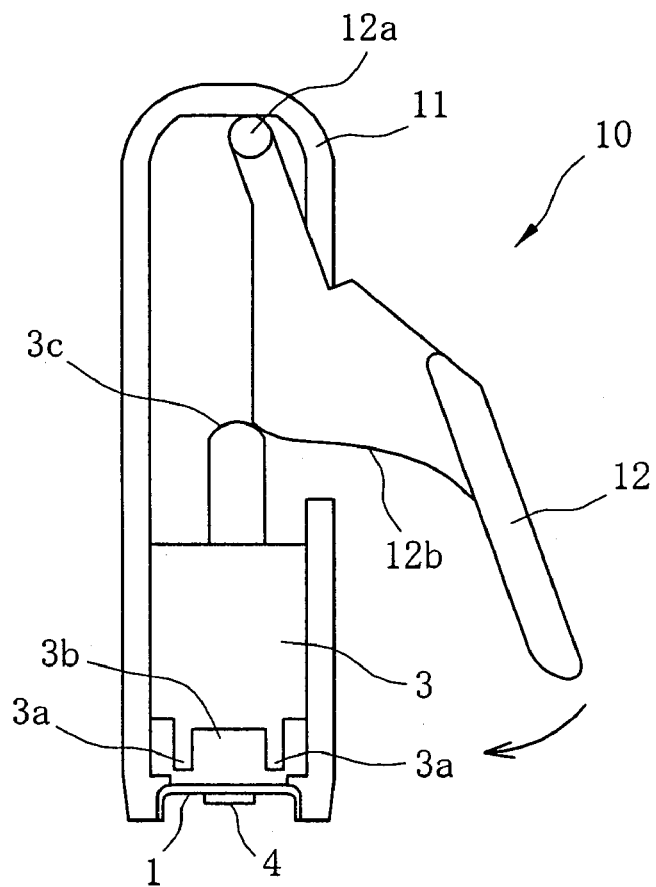
FIGS. 1A and 1B are diagrams showing the surgical stapler shown in the conventional example shown in FIG. 4 improved to achieve the object of the present invention, with FIG. 1A showing the surgical stapler prior to bending of the staple and FIG. 1B showing the surgical stapler in a state in which the bending of the staple is completed.
Figure 1B:
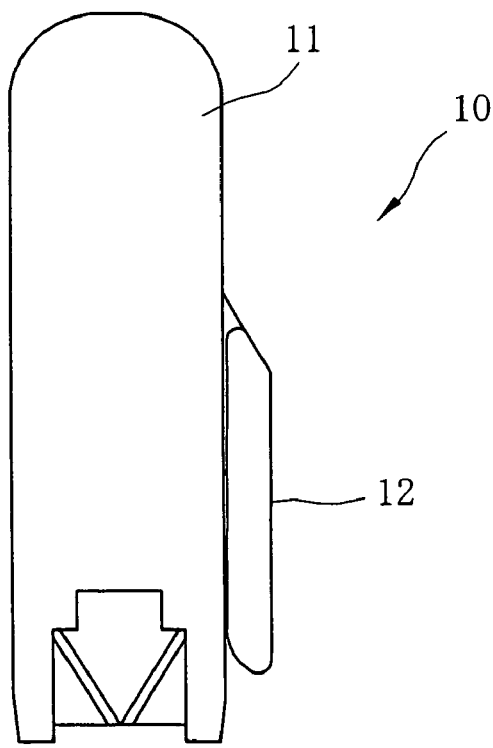
Figure 4:
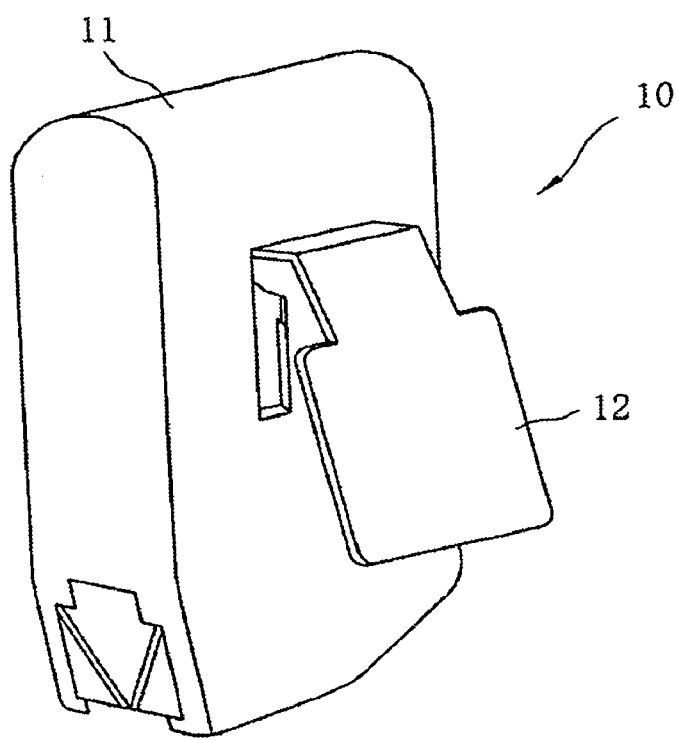
FIG. 4 is a diagram showing an external view of a conventional surgical stapler.

FIGS. 1A and 1B are diagrams showing the surgical stapler shown in the conventional example shown in FIG. 4 improved to achieve the object of the present invention, with FIG. 1A showing the surgical stapler prior to bending of the staple and FIG. 1B showing the surgical stapler in a state in which the bending of the staple is completed.

With a surgical stapler 10 shown in FIGS. 1A, 1B, one end of a trigger 12 is supported within a body 11 of the surgical stapler 10 so as to rotate freely. A plate cam 12b is formed on the trigger 12, and when the trigger 12 revolves clockwise around a shaft 12a, the plate cam 12b presses a projection 3c on a ram 3 and the ram 3 moves downward in the diagram. When the force applied to the trigger 12 is released, the ram 3 returns upward impelled by the force of a spring, not shown, and the trigger 12 revolves counterclockwise to return to its original position. A plurality of staples 1 are held so as to straddle an anvil 4, although in FIG. 1A only the first staple 1 is shown. This staple 1 is pushed in a direction perpendicular to the surface of the paper on which the diagram is drawn by a spring, not shown, and prevented from flying outward by a cover, not shown, that covers the body 11.

Figure 3A:
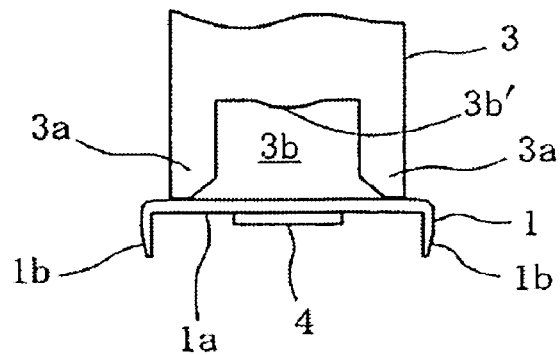
FIGS. 3A, 3B and 3C are diagrams showing the process of the surgical stapler bending the staple, showing the start, middle and end states of the stapling process, respectively.
Figure 3B:
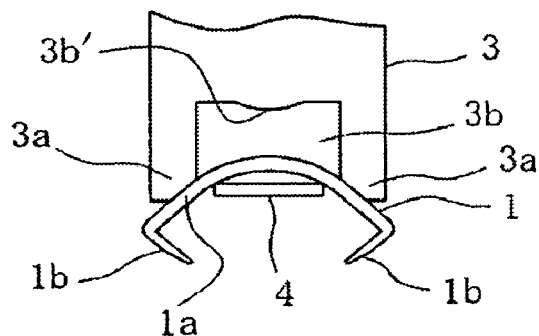
Figure 3C:
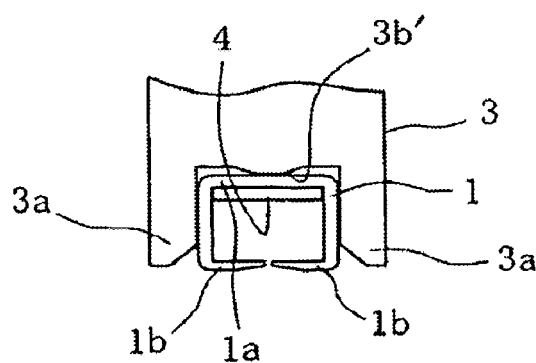

When a front edge of the trigger 12 is pressed and the trigger 12 rotated in the clockwise direction, the plate cam 12b presses the ram 3 downward, bending and closing the staple 1 into its final form as in the process shown in FIGS. 3A, 3B and 3C. Then, just before reaching the state shown in FIG. 3C, the load on the trigger 12 rapidly decreases and the rotation of the trigger quickens, completing the bending of the staple 1. In this embodiment of the present invention, when this bending is completed, the trigger 12 strikes the body 11 so as to produce a sound of impact. With such a construction, the user can sense clearly that the suture is complete, thus preventing incomplete suturing of an incision.

Figure 2A:
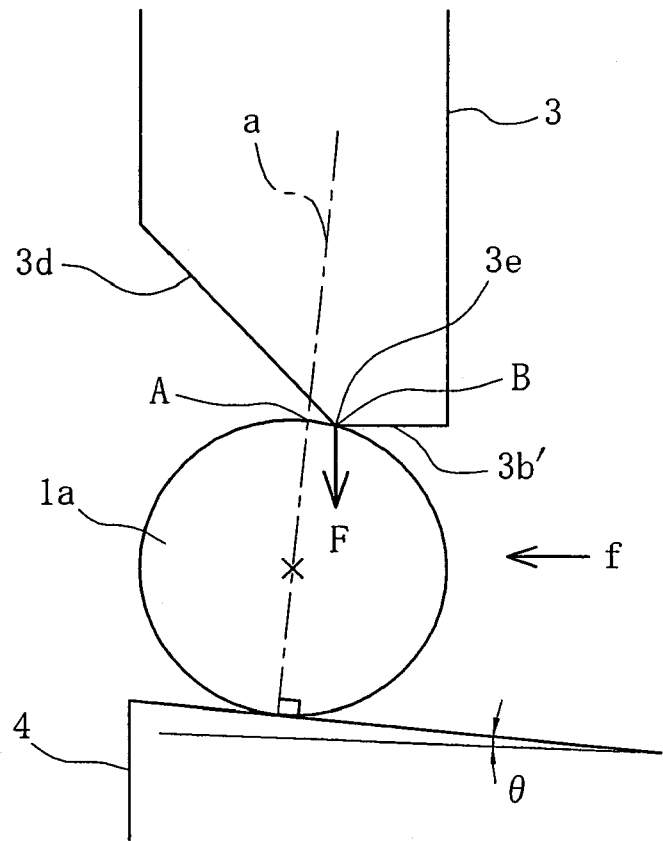
FIGS. 2A and 2B are diagrams showing a second embodiment of the present invention.
Figure 2B:
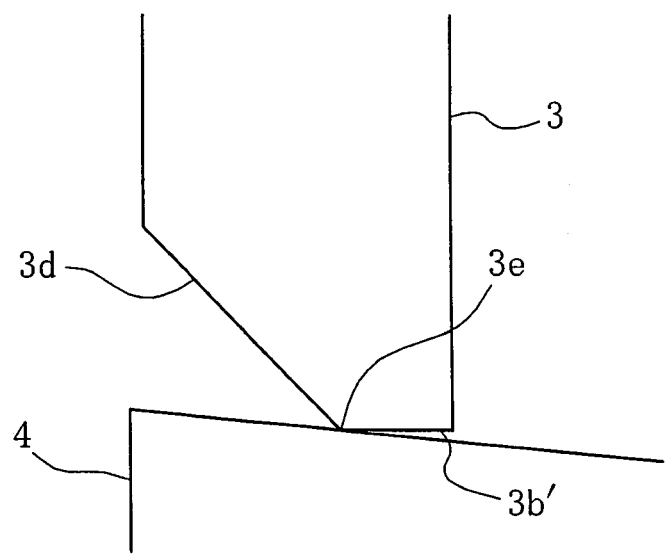
Figure 5:
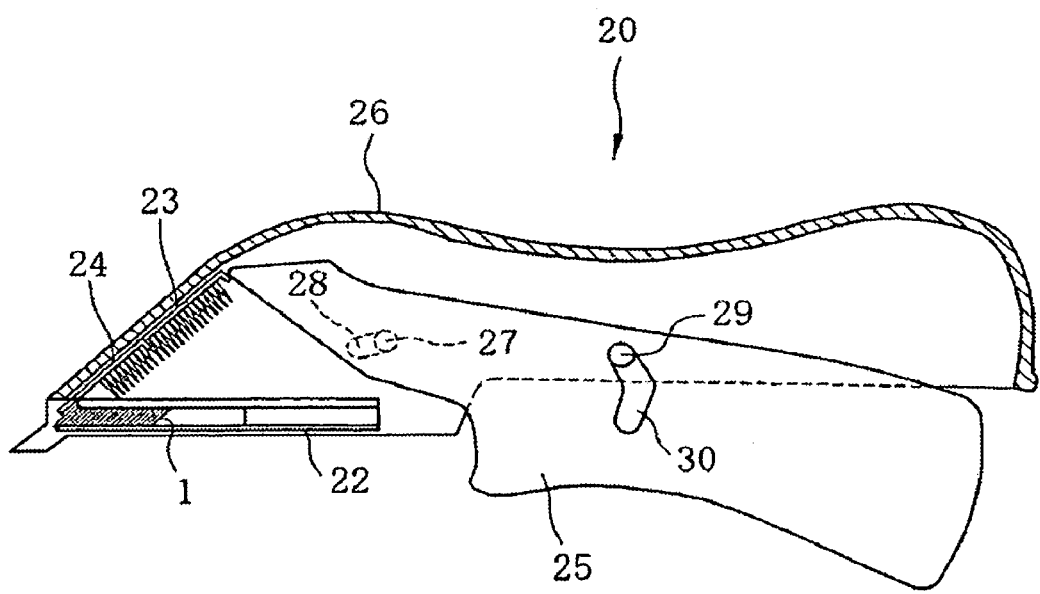
FIG. 5 is a diagram showing the structure of another conventional surgical stapler.

FIGS. 2A and 2B are diagrams showing a second embodiment of the present invention. In this embodiment, a slanted surface 3d is formed on a bottom surface 3b' of a concave portion of the ram 3, forming a ridge line 3e at the boundary between the bottom surface 3b' of the concave portion and the slanted surface 3d. The trigger may be any suitable form, including the trigger 12 shown in FIG. 4 or the trigger 25 shown in FIG. 5. The trigger 12 shown in FIG. 4 is used in the following description.

When force is applied to the trigger 12, the trigger 12 begins to revolve in the clockwise direction, the plate cam 12b of the trigger 12 presses on the projection 3c of the ram 3 and begins to push the ram 3. Soon, as shown in FIG. 3A, the tips of pressure armatures 3a contact the crown of the staple 1. Then, as the force applies to the trigger 12 continues to increase, the staple 1 begins to bend as shown in FIG. 3B. At this point, the force exerted on the trigger 12 and the degree of bending of the staple 1 increase substantially proportionally. When the force applied to the staple 1 increases to a certain level the staple 1 reaches its yielding point, after which the force applied to the trigger decreases and the staple continues to bend. At the stage at which the bending of the staple 1 is substantially completed as shown in FIG. 3C, the bottom surface 3b' strikes the crown of the staple 1 along the ridge line 3e. Thereafter, as further force is applied to the trigger 12, the force F exerted on the ram 3 increases. At the same time, a plurality of staples are contained within the surgical stapler and impelled to the left in FIG. 2A by a force f of a spring, not shown. A top surface of the anvil 4 is not level but inclined at an angle θ, with the forward edge thereof slanted upward.

While the force F is small, the staple 1 is pressed against the anvil 4 and the relative positions of the ram 3 and the anvil 4 do not change. However, once the force F exceeds a certain limit, the sum of the angular moment of the force F and the force f overcome the frictional force of the anvil 4 and the staple 1. At that moment, the ridge line 3e slips from point B off the outer peripheral surface of the staple 1 and the slanted surface 3d pushes the staple 1 to the left in the diagram, releasing the staple 1 from the anvil 4. At the same time, the ridge line 3e or the bottom surface 3b' of the ram 3 sharply strikes the anvil 4, producing for example a sharp metallic click or the like that is the sound of impact, by which the user of the surgical stapler can confirm that the suture is completed. Alternatively, a vibration may be produced instead of the sound of impact to achieve the same purpose.

It should be noted that, although in the above-described embodiments the ram 3 and the anvil 4 strike each other as to produce a sound or a vibration, alternatively, the surgical stapler may be constructed so that the ram 3 and the anvil 4 do not strike each other but instead remain a slight distance apart while the trigger 12 strikes the body 11 of the surgical stapler.

As many apparently widely different embodiments of the present invention can be made without departing from the spirit and scope thereof, it is to be understood that the invention is not limited to the specific preferred embodiments described above thereof except as defined in the claims.

What is claimed is:

1. A surgical stapler comprising:
    a body capable of containing a plurality of staples in an aligned state;
    a ram provided inside said body, having a central concave portion and pressure armatures on both sides of the concave portion;
    an anvil that, when the armatures of said ram contact both sides of a crown of a staple, forces the center of the crown into the concave portion of the ram; and
    a trigger rotatably supported on the body so as to cause relative movement between the ram and the anvil,
    wherein the staples are circular in cross-section, a front edge of a bottom surface of the concave portion of the ram has a slanted surface slanting outwardly in a direction away from the central concave portion of the ram, a ridge line of a front edge of said slanted surface contacting a staple on the anvil at a position offset to the rear of a center line of the staple.

* * * * *